(12) United States Patent
Trent et al.

(10) Patent No.: US 7,980,486 B2
(45) Date of Patent: Jul. 19, 2011

(54) MULTI-LAYER FILM COVERINGS FOR VOLATIZING DISPENSERS

(75) Inventors: John S. Trent, Franklin, WI (US); Anne T. Maghasi, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 107 days.

(21) Appl. No.: 12/430,349

(22) Filed: Apr. 27, 2009

(65) Prior Publication Data

US 2010/0270392 A1    Oct. 28, 2010

(51) Int. Cl.
*A24F 25/00* (2006.01)
(52) U.S. Cl. .......... 239/55; 239/34; 239/53; 239/60; 428/905; 206/484.1; 206/484.2
(58) Field of Classification Search .......... 239/34, 239/53, 55, 56, 60; 428/905; 206/484.1, 206/484.2
See application file for complete search history.

(56) References Cited

U.S. PATENT DOCUMENTS

| | | | |
|---|---|---|---|
| 4,055,672 A | 10/1977 | Hirsch et al. | |
| 4,128,508 A | 12/1978 | Munden | |
| 4,145,001 A | 3/1979 | Weyenberg et al. | |
| 4,824,917 A | 4/1989 | Kordomenos et al. | |
| 4,849,606 A | 7/1989 | Martens, III et al. | |
| 5,028,431 A * | 7/1991 | Franz et al. | 424/449 |
| 5,111,477 A | 5/1992 | Muderlak | |
| 5,395,047 A * | 3/1995 | Pendergrass, Jr. | 239/56 |
| 5,439,100 A * | 8/1995 | Gordon et al. | 239/60 |
| 5,518,790 A | 5/1996 | Huber et al. | |
| 5,637,401 A | 6/1997 | Berman et al. | |
| 5,647,052 A | 7/1997 | Patel et al. | |
| 5,782,409 A * | 7/1998 | Paul | 239/56 |
| 5,804,264 A | 9/1998 | Bowen | |
| 6,530,472 B2 | 3/2003 | Hacikyan | |
| 6,554,887 B1 | 4/2003 | Inglis | |
| 6,638,591 B2 | 10/2003 | Bowen et al. | |
| 6,663,838 B1 | 12/2003 | Soller et al. | |
| 6,722,578 B2 | 4/2004 | Skalitzky et al. | |
| 6,790,670 B2 | 9/2004 | Munagavalasa et al. | |
| 6,893,672 B2 | 5/2005 | Ingraham | |
| 6,902,817 B2 | 6/2005 | Bowen et al. | |
| 7,188,780 B2 | 3/2007 | Martens, III | |
| 7,213,770 B2 | 5/2007 | Martens, III et al. | |
| 7,419,677 B2 | 9/2008 | Gueret | |
| 2007/0183932 A1 | 8/2007 | Adair et al. | |
| 2008/0141928 A1 | 6/2008 | Adair et al. | |
| 2008/0172015 A1 | 7/2008 | Okada et al. | |

* cited by examiner

*Primary Examiner* — Steven J Ganey

(57) ABSTRACT

Disclosed are dispensers for volatile materials. There is a container in the form of a well having an internal cavity, a volatile chemical positioned in the cavity, and a multi-layer covering enclosing the cavity. The covering has a lower section that is gas permeable, and an upper section removably bound to the lower section that is not. Embodiments include when (a) the lower section has a top layer that is a blend of high density polyethylene and low density polyethylene; the upper section has a bottom layer that has a mixture of polypropylene and a propylene/ethylene copolymer; and/or the lower section has an upper layer that has low density polyethylene but the lower section does not contain ultra low density polyethylene. These features help prevent premature leakage at the bond between the upper section and lower section.

9 Claims, 4 Drawing Sheets

MULTI-LAYER FILM COVERINGS FOR VOLATIZING DISPENSERS

CROSS-REFERENCE TO RELATED APPLICATIONS

Not applicable.

STATEMENT REGARDING FEDERALLY SPONSORED RESEARCH/DEVELOPMENT

Not applicable.

BACKGROUND OF THE INVENTION

The present invention relates to coverings over containers that house volatile chemicals. More particularly it relates to multi-layer membranes which can divide into a gas permeable laminate that is permanently affixed to the container, and a peel-off gas impermeable layer.

A variety of volatiles are contained in containers that have a membrane closure. The closure is in the form of a multi-layer film structure configured such that a lower membrane section of the structure is permeable to the volatile when the volatile is in a gas phase, and is permanently affixed to an otherwise open end of the container. There is also an upper membrane section of the closure that is a peel-off type lid that is impermeable to the gas volatile. Before the lid is peeled off, the volatile is trapped in the container. When the lid is peeled off the volatile (to the extent in a gas phase) can begin to escape for its intended purpose. See e.g. U.S. Pat. Nos. 4,055,672, 4,849,606, 5,518,790 and 6,722,578, and U.S. patent application publication 2007/0183932.

The volatile is often an air treatment chemical such as insect control agents (insecticides, insect repellents, insect growth regulators, insect attractants, synergists, etc.), fragrances and deodorizers. However, it may also be a use-up indicator chemical whose volatilization rate has been coordinated with the use-up rate of an air treatment chemical that is also being volatized. Often the volatilization occurs when the container is heated by an external source of heat. However, the volatization may optionally occur even though no additional heat is applied.

Regardless, such systems are typically designed so that volatilization shouldn't begin prior to the consumer placing the product in use. Hence, it is important that a peel-off structure used to initiate these products have a sufficient seal to the permeable membrane so as to effectively prevent premature leakage of the volatile during storage prior to use. This is made somewhat more complicated by the need for the bond between the upper and lower sections of the structure to be sufficiently weak so that the upper section can readily be pulled off it without disturbing the bond between the lower section and the container.

Further complicating matters is that such structures are sometimes exposed to temperatures over 50° C. (e.g. in a transport truck in the desert during the summer). This can degrade certain bonds. Moreover, it has been learned that some preferred volatiles, especially under elevated temperature conditions, can act to further degrade the bond between the peel-off portion and the permanent permeable portion.

Thus, a need exists for improved multi-layer film coverings for volatizing dispensers, particularly where the coverings have a reduced risk of leakage prior to use.

BRIEF SUMMARY OF THE INVENTION

The invention provides dispensers for volatile materials. In one form there is a container in the form of a well having an internal cavity, a volatile chemical positioned in the cavity, and a multi-layer covering bound to the well. The covering has a lower/inward section that is sufficiently permeable to permit a gas form of the volatile chemical to pass through it, and an upper/outward section removably bound to the lower section that is essentially impermeable to the volatile chemical. When the upper section covers the lower section the volatile chemical can be trapped in the cavity, and when the upper section is peeled off from the lower section the volatile chemical can escape through the lower section out of the dispenser.

Three key embodiments of this structure are when:

(a) the lower section has a top layer that comprises a blend of high density polyethylene (often less than 50% by weight) and low density polyethylene;

(b) the upper section has a bottom layer that comprises a mixture of polypropylene and a propylene/ethylene copolymer (the latter preferably less than 30% by weight); and/or (c) the lower section has an upper layer that comprises low density polyethylene, but the lower section does not contain ultra low density polyethylene.

For example, preferred embodiments are where lower section has a top layer that comprises at least 5% (alternatively at least 20%) high density polyethylene. However, in those situations where a heater is to be used, the top layer can even be as high as 100% high density polyethylene.

In one aspect the volatile chemical is stored as a gel in the cavity, and is in the form of an indicator chemical, and the lower section is heat sealed to the well. The volatile could be one of a variety of air treatment chemicals and/or use-up cue indicator chemicals. Further, it can be a solid material prior to heating.

It will be appreciated that this covering includes a lower section that is sufficiently permeable to permit a gas form of the volatile to pass through it (while preventing passage of solid or liquid form of the chemical), and an upper section removably bound to the lower section that is essentially impermeable to the volatile. The upper section can be in the form of a peel-off strip.

It has been discovered that by carefully controlling polyethylene densities in specified layers of membrane(s) and/or by adding a particular type of copolymer at a facing layer, the tendency of the bond between upper and lower sections of the covering to degrade during storage can be reduced. This can be achieved while also retaining desirable permeation characteristics and appropriate peel-off characteristics. These advantages are achieved at relatively low additional cost, and without introducing significant manufacturing complexity.

The foregoing and other advantages of the present invention will be apparent from the following description. In that description reference is made to the accompanying drawings which form a part thereof, and in which there is shown by way of illustration, and not limitation, preferred embodiments of the invention. Such embodiments do not necessarily represent the full scope of the invention, and reference should therefore be made to the claims herein for interpreting the scope of the invention.

DETAILED DESCRIPTION OF THE PREFERRED EMBODIMENTS

Figure 1:
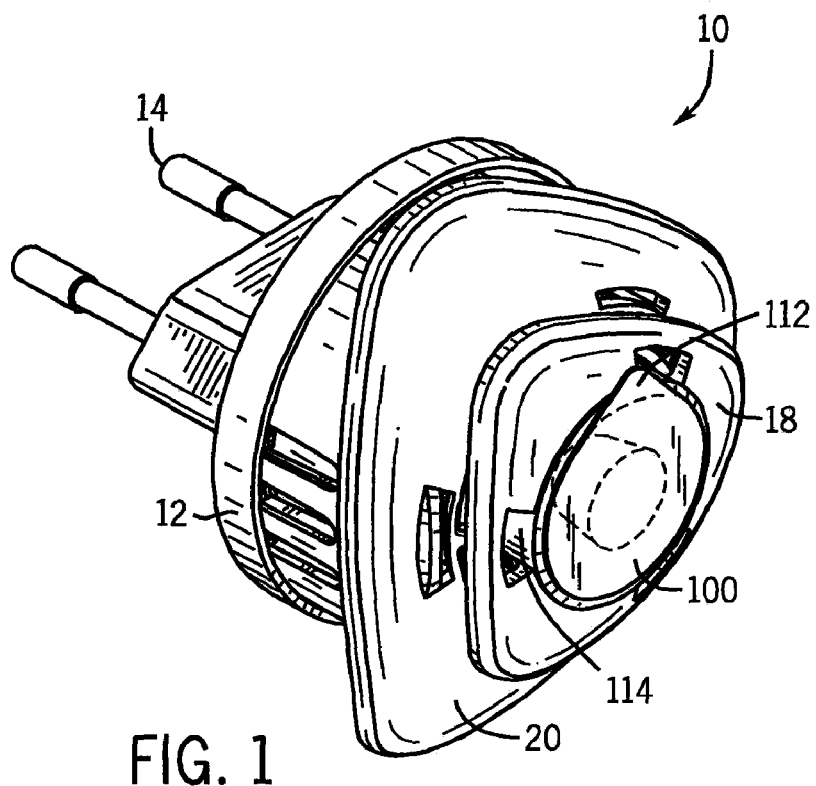
FIG. 1 is a prior art air treatment device that has positioned on its outward end a use-up indicator cartridge unit.
Figure 2:
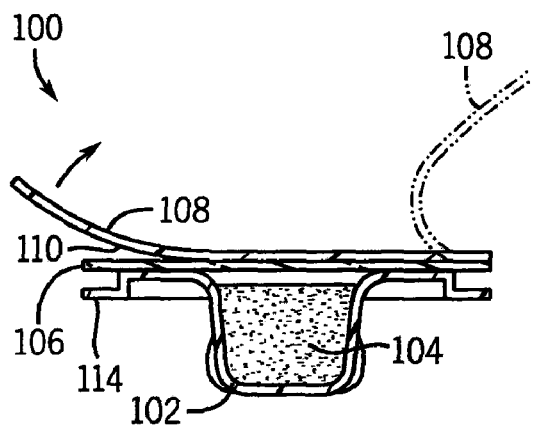
FIG. 2 is a sectional view through that indicator unit, showing how a peel-off layer can be removed so as to initiate volatilization of that use-up indicator unit.
Figure 3:
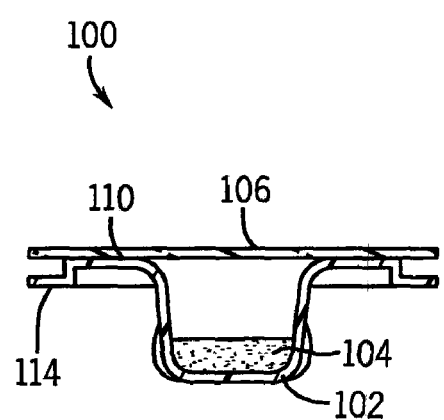
FIG. 3 is a view similar to FIG. 2, but after some of the indicator chemical has volatized.

FIG. 1 depicts a prior art air treatment device generally 10. It has a housing 12 that contains a heater (not shown) powered by contact prongs 14. The heater heats an impregnated substrate (not shown) to drive an air treatment chemical (e.g. an insect repellent or fragrance) out radial sides of the housing.

Mounted at the front of the device is a table 18 that can be snapped onto a front wall 20 of the structure. That device had a compact indicator unit 100 removably positioned in a recess of the table 18. The unit 100 had a cup-shaped storage well 102 for holding a volatile indicator chemical 104 in a cavity defined by the well.

A permeable multilayer membrane 106 encloses the well 102. By "permeable" it is meant that a gas phase of the volatile indicator chemical 104 can pass through the membrane 106, even though if in a solid or gel form (e.g. during storage) it cannot.

On top of membrane 106 is positioned a peel-off, essentially impermeable, multilayer membrane 108. This positioning is via a heat seal 110 or other conventional adhesive bond. By tugging at a tab portion 112 of membrane 108 that membrane 108 can be pulled off membrane 106, notwithstanding seal 110, while leaving membrane 106 securely bound to the well 102 (e.g. at a radial flange of the well). By "essentially impermeable" it is meant that when the seal 110 is in place a gas form of the chemical 104 cannot readily diffuse through membrane 108.

The nature of the membrane 106 and the chemical 104 are such that the rate of disappearance of the chemical 104 as to be coordinated with the rate of disappearance of the air treatment chemical inside the housing 12. This therefore provides a visual cue regarding when the air treatment chemical needs to be replaced. This is facilitated by making the wall of the well 102 transparent. For example, the well 102 can be made from heat-resistant polyethylene terephthalate in a transparent form. The indicator chemical could be volatile hydrocarbons such as Norpar brand normal paraffins like NORPAR™ 12, NORPAR™ 13, and NORPAR™ 15, or Isopar brand isoparaffinic hydrocarbons like ISOPAR™ L and ISOPAR™ M, or mixtures thereof.

Various other refinements have been proposed for such devices in the prior art, such as providing snap arms 114 to facilitate mounting of the unit 100. For further descriptions of prior art systems of this type see U.S. patent application publication 2007/0183932.

Figure 4:
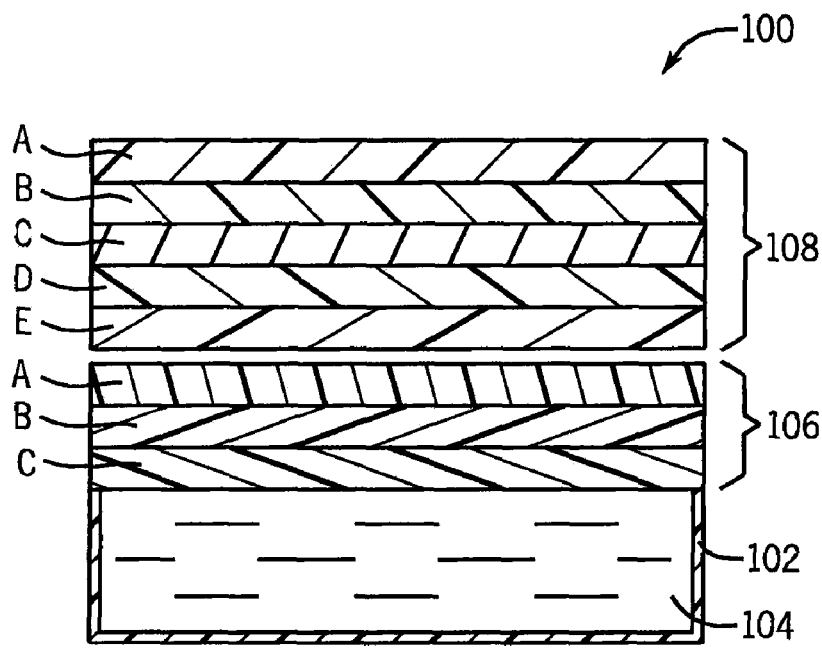
FIG. 4 is an enlarged detailed schematic view of a prior art multi-layer film covering used with a variety of dispensing devices.

As seen in FIG. 4, a gas permeable, permanently affixed membrane 106 covers a storage well 102 having an air treatment chemical 104 therein. The membrane 106 has a low density polyethylene layer 106A (preferably 0.5 mil thick), under which is positioned an ultra low density polyethylene layer 106B (preferably 2.5 mil thick), under which is positioned another low density polyethylene layer 106C (preferably 1.0 mil thick).

An essentially impermeable, removable/peel-off membrane 108 has a layer of polyester material 108A (used for reverse printing), under which is positioned a low density polyethylene material 108B (seal or adhesive layer), under which is positioned aluminum foil 108C (creating impermeability to the solvent), under which is positioned a layer of polypropylene material 108D, under which is positioned a cast form layer of polypropylene material 108E.

Turning now to FIGS. 5-11, there are disclosed a number of embodiments of the present invention. To better understand the terms being used in describing these embodiments the following definitions should be understood:

(a) A "polyester material" means a polymer which contains the ester functional group in its main chain. Although there are many polyesters made by replacing part of the terephthalic acid in the polymerization process with another acid, or part of the diol with another diol to produce polyester copolymers, the term "polyester" as a specific material most commonly refers to polyethylene terephthalate (PET) type materials. Polyesters include naturally-occurring chemicals, such as in the cutin of plant cuticles, as well as synthetics.

(b) An "ultra low density polyethylene material" ("ULDPE") means a form of polyethylene defined by a density range of 0.860 g/cm$^3$—just below 0.90 g/cm$^3$.

(c) A "linear low density polyethylene material" ("LLDPE") means a form of polyethylene defined by a density range of 0.90 g/cm$^3$—just below 0.94 g/cm$^3$.

(d) A "low density polyethylene material" ("LDPE") means a form of polyethylene defined by a density range of 0.91 g/cm$^3$—just below 0.94 g/cm$^3$.

(e) A "high density polyethylene material" ("HDPE") means a form of polyethylene defined by a density range of 0.94 g/cm$^3$-0.97 g/cm$^3$. Particularly desirable HDPE for mixing with conventional LDPE (as will be described below) are the high density polyethylene resins UNIVAL DMDA-6200NT7, 8007NT7 and 9804NT7.

(f) See generally for other polyethylene definitions, A. Peacock, Handbook of Polyethylene: Structures, Properties, and Applications, page 16, Marcel Dekker, Inc., New York, (2000).

Figure 5:
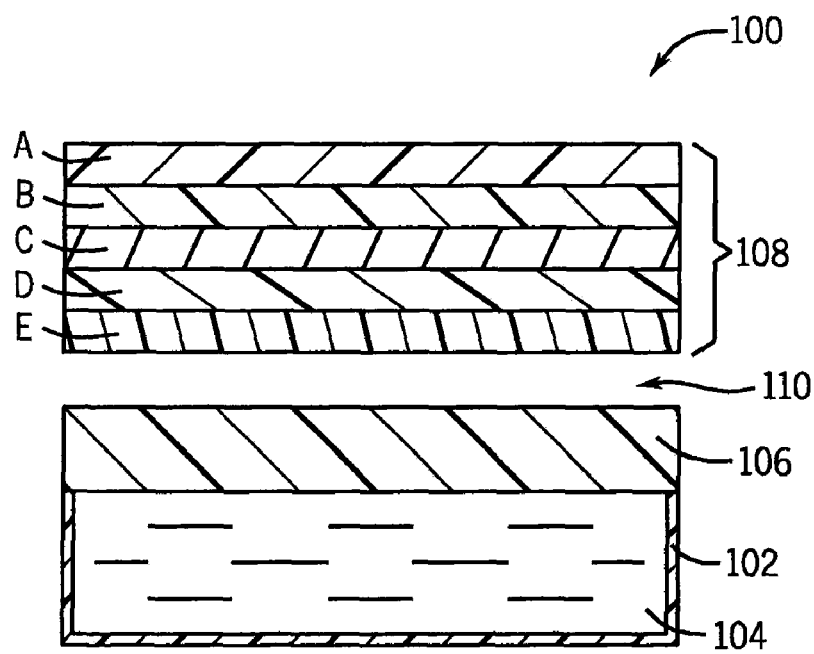
FIG. 5 is a view similar to FIG. 4, but of a device of the present invention.

In a first form of the invention (as depicted in FIG. 5) the impermeable membrane 108, and the well 102 are as shown in FIG. 4. However, the permanent membrane 106 now is a single 3 mil thick layer of LDPE, as distinguished from a thicker structure of FIG. 4, but without use of ULDPE.

Figure 6:
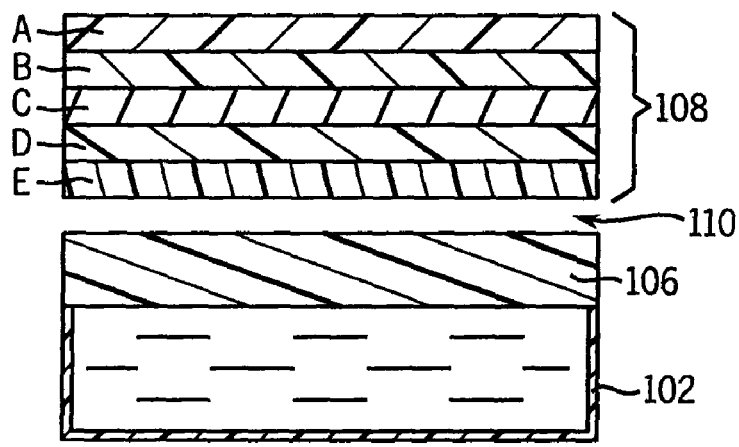
FIG. 6 is another view similar to FIG. 4, but of a second embodiment of the present invention.

FIG. 6 depicts a structure identical to FIG. 5, albeit in FIG. 6 we have made layer 108E a layer that contains 75% polypropylene blended with 25% of a propylene/ethylene copolymer. Suitable propylene/ethylene copolymers for use in this invention include the VERSIFY® family of copolymers available from Dow Chemical. This helps the bond resist degradation during storage, yet does not unduly interfere with the peel-off nature of the bond.

Figure 7:
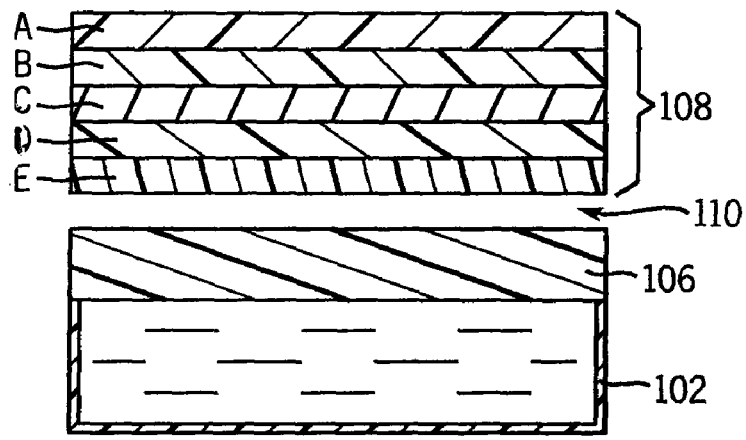
FIG. 7 is another view similar to FIG. 4, but of a third embodiment of the present invention.

FIG. 7 depicts a structure identical to FIG. 6, except that layer 108E now is either:

(a) a layer that contains 50% polypropylene blended with 50% propylene/ethylene copolymer; or (b) a layer that contains 25% polypropylene blended with 75% propylene/ethylene copolymer.

The layers 108E in FIGS. 6 and 7 are preferably 1 mil thick. It should be noted that the FIG. 6 construction is much preferred as compared to the FIG. 7 constructions. Less than 30% propylene/ethylene copolymer is preferred in the facing layer.

Figure 8:
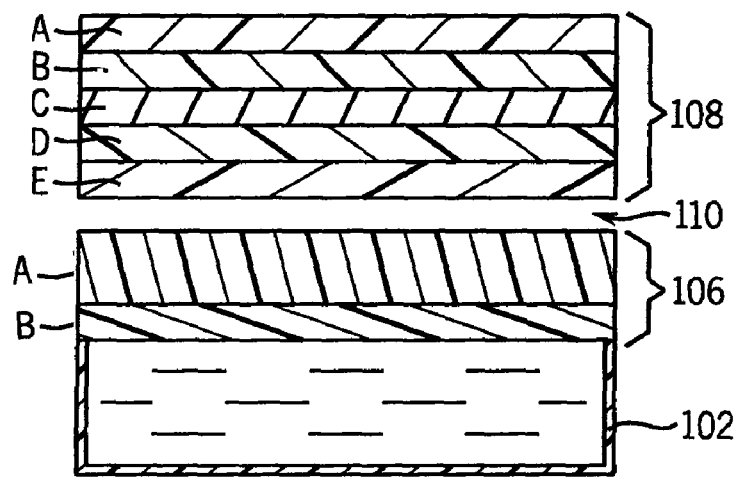
FIG. 8 is another view similar to FIG. 4, but of a fourth embodiment of the present invention.

In the FIG. 8 embodiment the membrane 108 is the same as in FIG. 5. However, here the membrane 106 is altered. The top layer 106A is now a structure which is a 90% LDPE/10% HDPE blend layer 106A approximately 3.0 mil thick. Positioned underneath that is a LDPE layer 106B that is 1.0 mils thick. Surprisingly, the higher density at layer 106A retards leakage, yet does not unduly affect permeation when desired.

Figure 9:
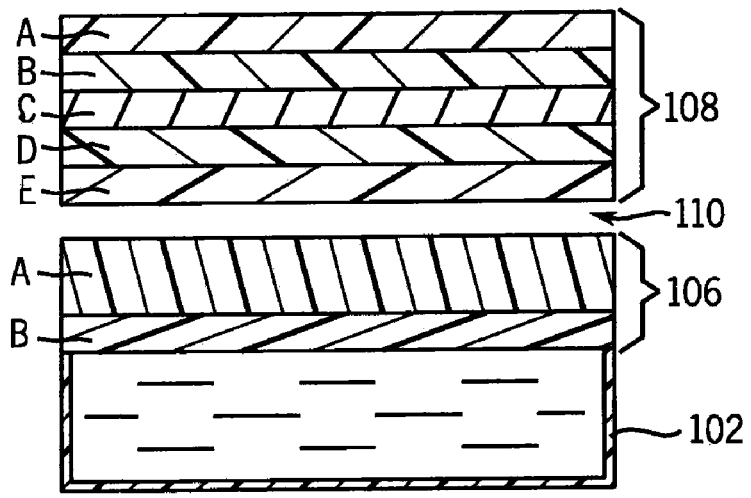
FIG. 9 is another view similar to FIG. 4, but of a fifth embodiment of the present invention.

FIG. 9 is identical to FIG. 8, albeit the layer 106A of the permeable membrane 106 comprises a 50% LDPE/50% HDPE material, and is again 3.0 mil thick. Increasing HDPE levels retards leakage, and correspondingly reduces permeation rates of solvent through the permeable layer 106.

Figure 10:
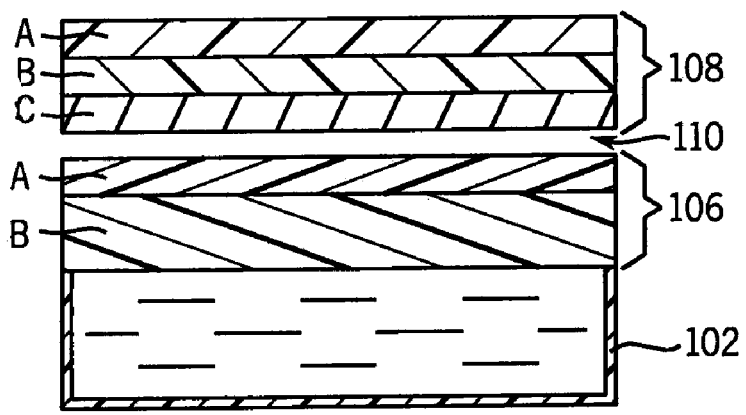
FIG. 10 is another view similar to FIG. 4, but of a sixth embodiment of the present invention.
Figure 11:
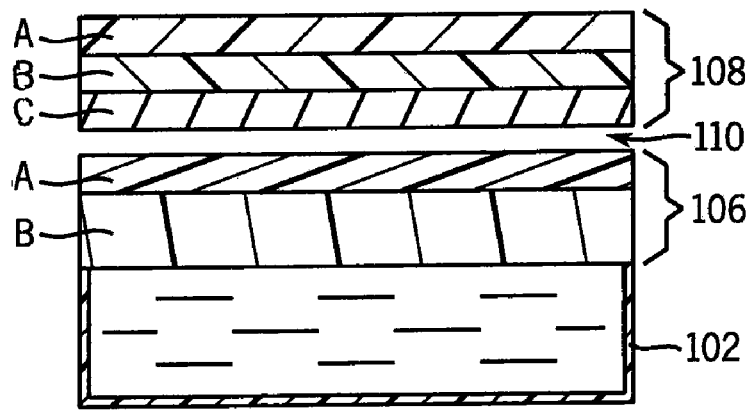
FIG. 11 is another view similar to FIG. 4, but of a seventh embodiment of the present invention.

In the FIG. 10 embodiment both membranes 106 and 108 are modified somewhat from the FIG. 5 structure. In this regard, the layer 106A is now split into a somewhat thicker layer 106A/106B structure. The layer 106A is normal blown film LDPE at 1.0 mil thick, and the layer 106B is a cast film of LDPE that is 3.0 mil thick.

However, here the membrane 108 is analogous to a structure having only layers 108A, 108B and 108C, except that the layer 108C is now metalized PET at 0.92 mils thick. This is a metalized polyethylene terephthalate (PET) material.

The FIG. 1 embodiment is identical to the FIG. 10 one, except that the layer 108B is now a more linear LLDPE, such as SABIC® LLDPE 118N.

The membranes 106 and 108 of the invention may be manufactured by many of various methods common in the art of making polymeric membranes. In one process, the layers may be coextruded. See also U.S. Pat. No. 6,902,817 for various other techniques of producing multi-layer laminates.

The two membranes 106 and 108 may be brought together over the storage well 102 with a heated die being applied to form heat bonds that bond the membrane 106 to the well, and assist in holding membrane 108 to membrane 106.

Test Results

The following table provides results of elevated temperature storage testing conducted at 54° C. for two weeks to illustrate the concepts of the present invention. A solvent mixture of hydrocarbons was stored in a well covered with varied combinations of permeable membranes covered by impermeable peel-off membranes. Leakage was evaluated after the two weeks.

| Test Variable | Top Layer Permeable Membrane | Bottom Layer Impermeable Membrane | Passes the Test (Y/N) |
| --- | --- | --- | --- |
| Standard | 1 mil LDPE/1 mil ULDPE/1 mil LDPE Blown Film | 1 mil PP | No |
| 1 | 3 mil LDPE Cast Film | 1 mil 75% PP/25% Versify | Yes |
| 2 | 3 mil 50% LDPE/50% HDPE | 1 mil PP | Yes |
| 3 | 3 mil 90% LDPE/10% HDPE | 1 mil PP | Yes |
| 4 | 3 mil LDPE Cast Film | 92 ga MET PET/7# LDPE | Yes |
| 5 | 3 mil LLDPE Blown Film | 92 ga MET PET/7# LDPE | Yes |

While preferred embodiments of the present invention have been described above, it should be appreciated that the invention could be used in a variety of other embodiments. For example, membranes 106 and 108 may each have more or less layers, and varied thicknesses. Also, varied chemicals can be added to the layers to alter permeation rates (e.g. adding filler such as calcium carbonate or talc).

Thus, the principles of the present invention can be applied in a variety of other ways apart from those specifically noted herein and/or depicted in the drawings. Such other modifications may be made without departing from the spirit and scope of the invention. Thus, the claims (rather than just the preferred embodiments) should be reviewed in order to understand the full scope of the invention.

INDUSTRIAL APPLICABILITY

Disclosed are improved multi-layer covering structures for use in controlling volatilization of air treatment chemicals and associated use-up indicators, which have reduced risk of premature leakage.

What is claimed is:
1. A dispenser for a volatile material, comprising:
a container in a form of a well having an internal cavity;
a volatile chemical positioned in the cavity; and
a multi-layer covering bound to the well, wherein the multi-layer covering has an inward section that is sufficiently permeable to permit a gas form of the volatile chemical to pass through it, and an outward section removably bound to the inward section that is essentially impermeable to the volatile chemical;
whereby when the outward section covers the inward section the volatile chemical can be trapped in the cavity, and when the outward section is peeled off from the inward section the volatile chemical can escape through the inward section out of the dispenser;
the dispenser further comprising that the outward section has an inward layer that is a mixture of polypropylene and a propylene/ethylene copolymer.

2. The dispenser of claim 1, wherein the inward layer of the outward section comprises no more than 30% by weight of the propylene/ethylene copolymer.

3. A dispenser for a volatile material, comprising:
a container in a form of a well having an internal cavity;
a volatile chemical positioned in the cavity; and
a multi-layer covering bound to the well, wherein the multi-layer covering has an inward section that is sufficiently permeable to permit a gas form of the volatile chemical to pass through it, and an outward section removably bound to the inward section that is essentially impermeable to the volatile chemical;
whereby when the outward section covers the inward section the volatile chemical can be trapped in the cavity, and when the outward section is peeled off from the inward section the volatile chemical can escape through the inward section out of the dispenser;
the dispenser further comprising that the inward section has an outward layer that comprises low density polyethylene, and the inward section does not include ultra low density polyethylene.

4. The dispenser of claim 3, wherein the outward layer of the inward section comprises at least 5% high density polyethylene.

5. The dispenser of claim 4, wherein the inward section has an outward layer that comprises at least 20% high density polyethylene.

6. The dispenser of claim 5, wherein the inward section has an outward layer that comprises no more than 50% high density polyethylene.

7. The dispenser of claim 4, wherein the outward section has an inward layer facing the inward section which comprises polypropylene.

8. The dispenser of claim 4, wherein the volatile chemical is stored as a gel in the cavity, and is in a form of an indicator chemical.

9. The dispenser of claim 4, wherein the inward section is heat sealed to the well.

* * * * *